United States Patent [19]
Ouchi

[11] Patent Number: 4,784,464
[45] Date of Patent: Nov. 15, 1988

[54] ENDOSCOPE OPTICAL FIBER BUNDLE

[75] Inventor: Teruo Ouchi, Tokyo, Japan

[73] Assignee: Asahi Kogaku Kogyo Kabushiki Kaisha, Tokyo, Japan

[21] Appl. No.: 10,616

[22] Filed: Feb. 4, 1987

[30] Foreign Application Priority Data

Feb. 4, 1986 [JP] Japan .................................. 61-23634

[51] Int. Cl.$^4$ ............................................. G02B 23/26
[52] U.S. Cl. ................................. 350/96.26; 350/96.24
[58] Field of Search ............... 350/96.23, 96.24, 96.25, 350/96.26

[56] References Cited

FOREIGN PATENT DOCUMENTS

| 0159607 | 12/1981 | Japan | 350/96.24 |
| 0104105 | 6/1982 | Japan | 350/96.24 |
| 0030504 | 2/1984 | Japan | 350/96.24 |

*Primary Examiner*—John D. Lee
*Assistant Examiner*—John Ngo
*Attorney, Agent, or Firm*—Sughrue, Mion, Zinn Macpeak, and Seas

[57] ABSTRACT

A fiber optic endoscope in which a bundle of optical fibers are sealed in a flexible cover tube with a lubricant. The cross section of the central part of the cover tube is about 62% of the cross section of the optical fibers when tightly bundled.

11 Claims, 2 Drawing Sheets

ENDOSCOPE OPTICAL FIBER BUNDLE

BACKGROUND OF THE INVENTION

1. Field of the Invention

This invention relates to observing or illuminating optical fiber bundles for endoscopes. More particularly, it relates to an endoscope optical fiber bundle which is made both suitably flexible and rigid to improve its durability.

2. Background of the Invention

In general, an endoscope optical fiber bundle is covered by a flexible cover tube. If the inside diameter of the cover tube is relatively close to the outside diameter of the optical fiber bundle, the assembly of the optical fiber bundle and the cover tube is so stiff, resembling a bar, that the optical fibers are liable to be broken when bent.

Therefore, heretofore, the optical fiber bundle is so designed that the sectional area s of the optical fibers bundled tight is about half (½) of the sectional area S of the hollow of the cover tube which is made circular in section i.e. $s=0.50S$.

As was described above, the conventional endoscope optical fiber bundle is loosely inserted into the cover tube to the extent that the relation $s=0.50S$ is established. Therefore, the assembly of the optical fiber bundle and the cover tube can be readily and smoothly bent. However if, when a flexible tube a of an endoscope or a bending part b connected to the flexible tube a is bent with a small radius of curvature as shown in FIG. 4, an optical fiber bundle c is on the inner edge of the curve. It is then possible that the optical fiber bundle c is bent in a zigzag and is buckled. Therefore, if this operation is repeatedly carried out, the fibers are broken, thus obstructing the observation or illumination.

SUMMARY OF THE INVENTION

Accordingly, an object of this invention is to provide an endoscope optical fiber bundle in which the above-described difficulties accompanying a conventional endoscope optical fiber bundle have been eliminated.

More specifically, an object of the invention is to provide an endoscope optical fiber bundle high in durability which, even if bent, is rarely broken and rarely buckles in the bending part or the like of the flexible tube of the endoscope.

In order to solve the above-described problems, the inventor has conducted intensive research on the endoscope optical fiber bundle and has found that the conventional endoscope optical fiber bundle buckles and its optical fibers consequently break because the optical fiber bundle is too flexible and not rigid. He also has found that the percentage of breakage of the optical fibers can be considerably reduced by giving appropriate flexibility and rigidity to the optical fiber bundle. Based on this finding, the inventor has accomplished this invention.

DETAILED DESCRIPTION OF THE PREFERRED EMBODIMENTS

One embodiment of this invention will be described with reference to FIGS. 1 through 3.

Figure 3:
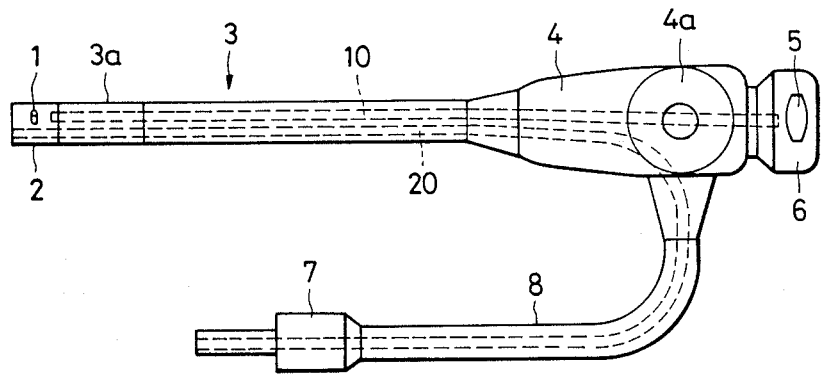
FIG. 3 is an explanatory diagram outlining the entire arrangement of an endoscope in which an endoscope optical fiber bundle of the invention is inserted.
Figure 4:
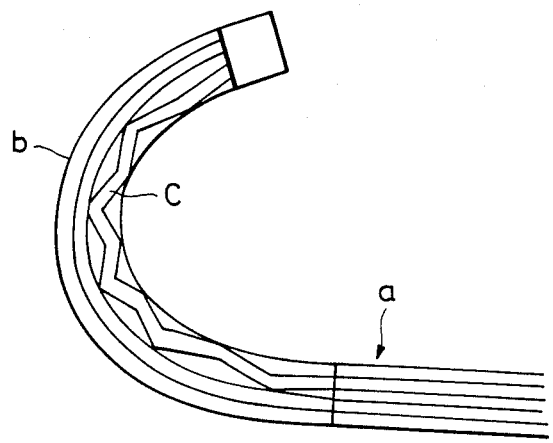
FIG. 4 is an explanatory diagram outlining conventional endoscope optical fiber bundles inserted into the flexible tube of an endoscope.
Figure 5:
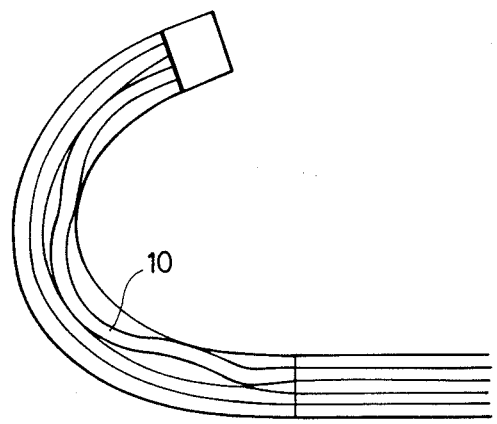
FIG. 5 is an explanatory diagram showing the endoscope optical fiber bundles of the invention in the flexible tube of an endoscope.

FIG. 3 is a diagram outlining the entire arrangement of an endoscope which employs endoscope optical fiber bundles according to the invention. As shown in FIG. 3, an end structure 2 incorporating an objective lens 1 is connected to one end of a flexible tube 3. The other end (or base end) of the flexible tube 3 is coupled to an operating part 4 including various operating devices. The top end portion of the flexible tube 3 is formed into a bending part 3a which can be bent by remotely operating an operating knob 4a of an operating part 4. The operating part 4 is connected to an eyepiece part 6 including an eyepiece 5 and is also connected to a flexible coupling tube 8 having a connector 7 at the other end. The connector 7 is connected to a lgith source (not shown).

Two endoscope optical fiber bundles, namely, an image transmitting optical fiber bundle 10 and an illuminating optical fiber bundle 20 are inserted into the flexible tube 3. The top end of the image transmitting optical fiber bundle 10 is held at the image forming position of the objective lens and its base end is held at the observing position of the eyepiece 5. The top end of the illuminating optical fiber bundle 20 is connected to the end structure 2 and the base end is secured to the end of the connector 7.

Figure 1:
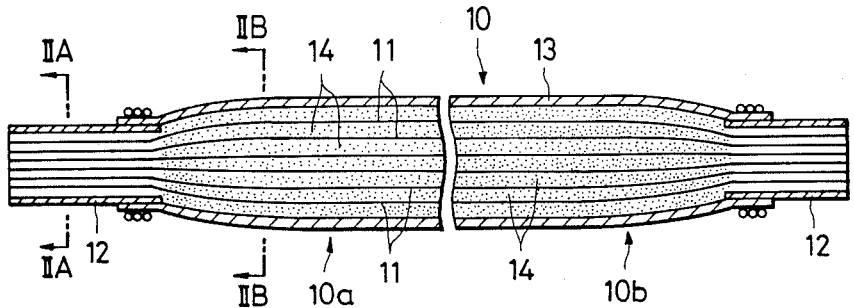
FIG. 1 is a longitudinal sectional view of an image transmitting optical fiber bundle which is one embodiment of this invention.

FIG. 1 is a longitudinal sectional view of the image transmitting optical fiber bundle 10. The optical fiber bundle 10 is formed by bundling several thousands to several tens of thousands of optical fibers 11 each having a diameter of 0.01 mm. The optical fiber bundle has both end portions tightly bundled, and the two end portions are fixedly inserted into respective mouth rings 12. The arrangement of the optical fibers at one end of the optical fiber bundle 10 is completely equal to that of the optical fibers at the other end so that a light beam applied to the one end of the optical fiber bundle 10 is correctly transmitted to the other end. Further in FIG. 1, a flexible cover tube 13 is made of a thin silicon tube. The image transmitting optical fiber bundle 10 is covered, substantially over its entire length, by the cover tube 13. Both ends of the cover tube 13 are coupled to the two mouth rings 12.

Inside the cover tube 13, the optical fibers 11 are not bonded together. That is, the cover tube 13 is filled with a lubricant 14 of molybdenum disulfide particles so that the friction between the optical fibers 11 is reduced. Moreover, in order to increase the durability of the optical fiber bundle 10 against the bending operation which is repeatedly applied to the optical fiber bundle 10, for instance, inside the bending part 3a of the endoscope flexible tube 3, the quantity of lubricant 14 at the end portion 10a of the optical fiber bundle 10 is made larger than that at the remaining portion. Alternatively, the cover tube 13 may be filled with the lubricant 14 in such a manner that the quantities of lubricant 14 at both end portions 10a and 10b of the optical fiber bundle 10 are larger than in the remaining portion. This method can be eliminate the difficulty that the optical fibers are broken during the endoscope assembly.

In the above-described embodiment, the lubricant 14 is not merely sealed in the cover tube. For instance, the lubricant 14 is directly applied to the optical fibers 11 with a brush, or the lubricant 14, after being mixed with volatile solution, is applied to the optical fibers 11. Then, the optical fibers 11 are inserted and sealed into the cover tube 13. If the lubricant is merely sealed in the cover tube, then the optical fibers are particularly brought into direct contact with one another, as a result of which, when the optical fibers are repeatedly bent, they may be broken. However, the above-described method of directly applying the lubricant 14 to the optical fibers 11 can completely eliminate the above-described difficulty.

The illuminating optical fiber bundle 20 is equivalent in construction to the above-described image transmitting optical fiber bundle 10 except that the arrangement of its optical fibers at one end does not need to be made coincident with that of the optical fibers at the other end. Therefore, the detailed description of the optical fiber bundle 20 will be omitted.

Figures 2A, 2B:
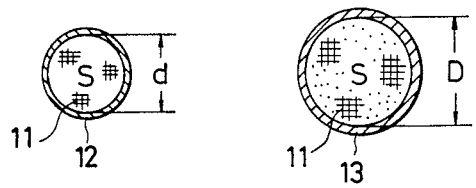
FIGS. 2(A) and 2(B) are sectional views taken along line IIA—IIA and IIB—IIB in FIG. 1, respectively.

FIG. 2(A) is a sectional view taken along line IIA—IIA in FIG. 1, showing the mouth ring 12 and the optical fibers 11. FIG. 2(B) is also a sectional view taken along lines IIB—IIB in FIG. 1, showing the cover tube 13 and the optical fibers 11 inserted thereinto. In FIG. 2(A), reference characters d and s respectively designate the diameter and the sectional area of the bundle of optical fibers 11 in the mouth ring 12, respectively. In FIG. 2(B), reference characters D and S designate the diameter and the sectional area of the interior of the cover tube 13 which is made circular in section.

SPECIFIC EXAMPLE 1

With respect to the above-described embodiment of the invention, a series of tests were performed with an image transmitting optical fiber bundle having an outside diameter d=1 mm (s=0.785 mm$^2$) and other ordinary compnenets were inserted in a bronchoendoscope having a flexible pipe 5 mm in diameter. In each test in the series, the bending part was bent 180° up and down 10,000 times. Different tests were carried out with the dimension of the cover tube of the image transmitting optical fiber bundle being changed. The test detected the breakage of the optical fibers of the image transmitting optical fiber bundle. The results of the tests are as indicated below.

| Cover tube | Fiber breakage |
|---|---|
| D = 1.50 mm (s = 0.44S) | X |
| D = 1.40 mm (s = 0.51S) | X |
| D = 1.35 mm (s = 0.55S) | O |
| D = 1.30 mm (s = 0.59S) | O |
| D = 1.25 mm (s = 0.64S) | O |
| D = 1.20 mm (s = 0.69S) | O |
| D = 1.15 mm (s = 0.76S) | XX |

Legend:
O — The fibers were not broken at all, or they were scarcely broken.
X — Some of the fibers were broken, and the use of the endoscope may have been unpractical.
XX — Most of the fibers were broken, the endoscope could not be used any longer.

SPECIFIC EXAMPLE 2

A series of tests were performed with an image transmitting optical fiber bundle having an outside diameter d=2 mm (s=3.14 mm$^2$) and other ordinary components were inserted in a duodenum endoscope. In each test in the series, the bending part was bent 140° up and down and 100° right and left 10,000 times. Different tests were performed with the dimension of the cover tube of the image transmitting optical fiber bundle being changed. The tests detected the breakage of the optical fibers of the image transmitting optical fiber bundle. The results of the tests are as indicated below.

| Cover tube | Fiber breakage |
|---|---|
| D = 3.0 mm (s = 0.44S) | XX |
| D = 2.8 mm (s = 0.51S) | X |
| D = 2.7 mm (s = 0.55S) | O |
| D = 2.6 mm (s = 0.59S) | O |
| D = 2.5 mm (s = 0.64S) | O |
| D = 2.4 mm (s = 0.69S) | Y |
| D = 2.3 mm (s = 0.76S) | XX |

Legend:
O — The fibers were not broken at all, or they were scarcely broken.
Y — A few of the fibers were broken, but the endoscope could be used with no trouble.
X — Some of the fibers were broken, and the use of the endoscope may have been unpractical.
XX — Most of the fibers were broken, the endoscope could not be used any longer.

SPECIFIC EXAMPLE 3

Another series of tests were performed with an image transmitting optical fiber bundle having a terminal outside diameter d=3 mm (s=7.07 mm$^2$) and other ordinary components were inserted into a bowel endoscope. In each test in the series, the bending part was bent 180° vertically and horizontally 10,000 times. Different tests were performed with the dimension of the cover tube of the image transmitting optical fiber bundle being changed. The tests detected the breakage of the optical fibers of the image transmitting optical fiber bundle. The results of the test are as follows:

| Cover tube | Fiber breakage |
|---|---|
| D = 4.50 mm (s = 0.44S) | XX |
| D = 4.20 mm (s = 0.51S) | X |
| D = 4.05 mm (s = 0.55S) | Y |
| D = 3.90 mm (s = 0.59S) | O |
| D = 3.75 mm (s = 0.64S) | O |
| D = 3.60 mm (s = 0.69S) | Y |
| D = 3.45 mm (s = 0.76S) | XX |

Legend:
O — The fibers were not broken at all, or they were scarcely broken.
Y — A few of the fibers were broken, but the endoscope could be used with no trouble.
X — Some of the fibers were broken, and the use of the endoscope may have been unpractical.
XX — Most of the fibers were broken, the endoscope could not be used any longer.

In the above-described specific examples, the image transmitting optical fiber bundles have been tested as typical examples of the endoscope optical fiber bundle. However, it should be noted that the invention is not limited thereto or thereby. That is, the results of the specific examples may be applicable to the illuminating optical fiber bundles.

As is apparent from the above description, the endoscope optical fiber bundle according to the invention is flexible to the extent that the optical fiber bundle is repeatedly bent in the flexible tube of the endoscope or the like, it is seldom broken. That is, the optical fiber bundle of the invention is considerably high in durability.

Furthermore, since the cover tube is not loose, the optical fiber bundle of the invention is free from the difficulty that the cover tube is clamped and broken by the bending part of the flexible tube of the endoscope. This also proves that the endoscope optical fiber bundle of the invention is excellent in durability.

What is claimed is:

1. An optical fiber endoscope, comprising:
   a flexible outer tube;
   a flexible cover tube inserted in said outer tube and having a middle substantially circular portion of sectional area S;
   a plurality of optical fibers inserted and sealed over substantially their entire length in said cover tube; and
   a lubricant sealed in said cover tube;
   wherein a sectional area s of said plurality of optical fibers when tightly bundled satisfies the relation $0.55S \leq s \leq 0.69S.$ 2. An endoscope as recited in claim 1, wherein said relation is restricted to $0.59S \leq s \leq 0.64S.$ 3. An endoscope as recited in claim 1, wherein a density of said lubricant at an operating end of said cover tube is greater than a density of said lubricant in a remaining portion of said cover tube.

4. An endoscope as recited in claim 2, wherein a density of said lubricant at an operating end of said cover tube is greater than a density of said lubricant in a remaining portion of said cover tube.

5. An endoscope as recited in claim 1, wherein densities of said lubricant in both end portions of said cover tube are greater than a density of said lubricant in an intermediate portion of said cover tube between said end portions.

6. An endoscope as recited in claim 2, wherein densities of said lubricant in both end portions of said cover tube are greater than a density of said lubricant in an intermediate portion of said cover tube between said end portions.

7. An endoscope as recited in claim 1, wherein said optical fibers are coated with said lubricant.

8. An endoscope as recited in claim 2, wherein said optical fibers are coated with said lubricant.

9. An endoscope as recited in claim 1, further comprising two rings each fixing said plurality of optical fibers with cross sectional areas substantially equal to s and sealingly held by ends of said cover tube.

10. An endoscope as recited in claim 2, further comprising two rings each fixing said plurality of optical fibers with cross sectional areas substantially equal to s and sealingly held by ends of said cover tube.

11. An endoscope as recited in claim 1, wherein said lubricant is coated on said fibers.

* * * * *